(12) United States Patent
Delfosse et al.

(10) Patent No.: US 10,843,201 B2
(45) Date of Patent: Nov. 24, 2020

(54) TWO STAGE GRINDER PARTICULARLY SUITABLE FOR MEDICAL WASTE DISPOSAL

(71) Applicants: Spectrum Medical Lending, LLC, Chicago, IL (US); Susan Rees Bates, Sudbury, MA (US)

(72) Inventors: Duane Delfosse, Windham, NH (US); Jeffrey H. Bell, Sudbury, MA (US); Peter G. Bates, Concord, MA (US)

(73) Assignee: Spectrum Medical Lending, LLC, Chicago, IL (US)

( * ) Notice: Subject to any disclaimer, the term of this patent is extended or adjusted under 35 U.S.C. 154(b) by 264 days.

(21) Appl. No.: 15/723,653

(22) Filed: Oct. 3, 2017

(65) Prior Publication Data

US 2018/0104700 A1   Apr. 19, 2018

Related U.S. Application Data

(60) Provisional application No. 62/403,430, filed on Oct. 3, 2016.

(51) Int. Cl.
| | |
|---|---|
| *B02C 18/00* | (2006.01) |
| *B02C 18/14* | (2006.01) |
| *B02C 19/00* | (2006.01) |
| *B09B 3/00* | (2006.01) |
| *A61M 5/32* | (2006.01) |
| *A61B 50/36* | (2016.01) |
| *B02C 18/24* | (2006.01) |
| *B02C 18/16* | (2006.01) |

(Continued)

(52) U.S. Cl.
CPC ............ *B02C 18/146* (2013.01); *A61B 50/36* (2016.02); *A61B 50/362* (2016.02); *A61M 5/3205* (2013.01); *B02C 18/142* (2013.01); *B02C 18/16* (2013.01); *B02C 18/182* (2013.01); *B02C 18/24* (2013.01); *B02C 19/0075* (2013.01); *B09B 3/0075* (2013.01); *B09B 3/0083* (2013.01); *B09B 5/00* (2013.01); *A61B 2017/00398* (2013.01); *A61B 2050/364* (2016.02); *B02C 2018/147* (2013.01); *B02C 2018/166* (2013.01)

(58) Field of Classification Search
CPC ........ B02C 2018/147; B02C 2018/166; B02C 18/142; B02C 18/182; B02C 18/42
USPC ...................... 241/152.2, 155, 158
See application file for complete search history.

(56) References Cited

U.S. PATENT DOCUMENTS 3,931,935 A * 1/1976 Holman ................ B02C 17/002
241/24.1
4,156,508 A * 5/1979 Kisielewski .......... B02C 18/142
209/284

(Continued)

*Primary Examiner* — Faye Francis
(74) *Attorney, Agent, or Firm* — Davis, Malm & D'Agostine, P.C.; Richard L. Sampson

(57) ABSTRACT

Featured are a two-stage grinder, an apparatus embodying same and methods related thereto. Such a medical waste grinder includes a first stage and a second stage. The first stage includes spring loaded cutter stacks mounted on two adjacent shafts between two edge plates, each of the cutter stacks including cutters arranged in a helix to create space, each cutter including a number of teeth per blade and including a major diameter and a minor diameter, each cutter turning opposite a fixed counter knife enabling a pinching action against the teeth of the cutter. The second stage includes spring loaded cutter stacks.

11 Claims, 5 Drawing Sheets

(51) Int. Cl.
  *B02C 18/18* (2006.01)
  *B09B 5/00* (2006.01)
  *A61B 17/00* (2006.01)

(56) References Cited

U.S. PATENT DOCUMENTS

| | | | |
|---|---|---|---|
| 4,607,800 A * | 8/1986 | Barclay | B02C 18/0084 241/159 |
| 5,462,238 A * | 10/1995 | Smith | B02C 18/2216 241/243 |
| 5,562,255 A * | 10/1996 | Witko | B02C 18/142 241/158 |
| 5,609,307 A * | 3/1997 | Rota | B02C 18/142 241/73 |
| 5,906,322 A * | 5/1999 | Hama | B02C 18/02 241/152.2 |
| 6,058,822 A * | 5/2000 | Parke | B02C 18/142 241/166 |
| 7,032,850 B2 * | 4/2006 | Fukui | B02C 13/02 241/159 |
| 7,168,639 B2 * | 1/2007 | Craft | B02C 18/146 241/223 |
| 7,534,392 B1 * | 5/2009 | Kodis | A61L 2/22 241/15 |
| 7,658,343 B2 * | 2/2010 | Potts | B02C 4/18 241/158 |
| 7,938,347 B2 * | 5/2011 | Romanovich | B02C 18/142 241/101.4 |
| 9,844,783 B2 * | 12/2017 | Bihn | B02C 4/06 |
| 10,086,380 B2 * | 10/2018 | Yamamoto | B02C 18/0007 |
| 2002/0023977 A1 * | 2/2002 | Nakagomi | B02C 18/142 241/236 |
| 2008/0265072 A1 * | 10/2008 | Wang | B02C 18/146 241/220 |
| 2010/0044487 A1 * | 2/2010 | Labbe | B02C 18/146 241/293 |
| 2011/0297767 A1 * | 12/2011 | Jiang | B02C 18/0007 241/34 |
| 2011/0297772 A1 * | 12/2011 | Pan | B02C 18/0007 241/101.2 |
| 2015/0041576 A1 * | 2/2015 | Romanovich | B02C 18/146 241/236 |
| 2016/0121336 A1 * | 5/2016 | Yalin | B02C 15/006 241/117 |

* cited by examiner

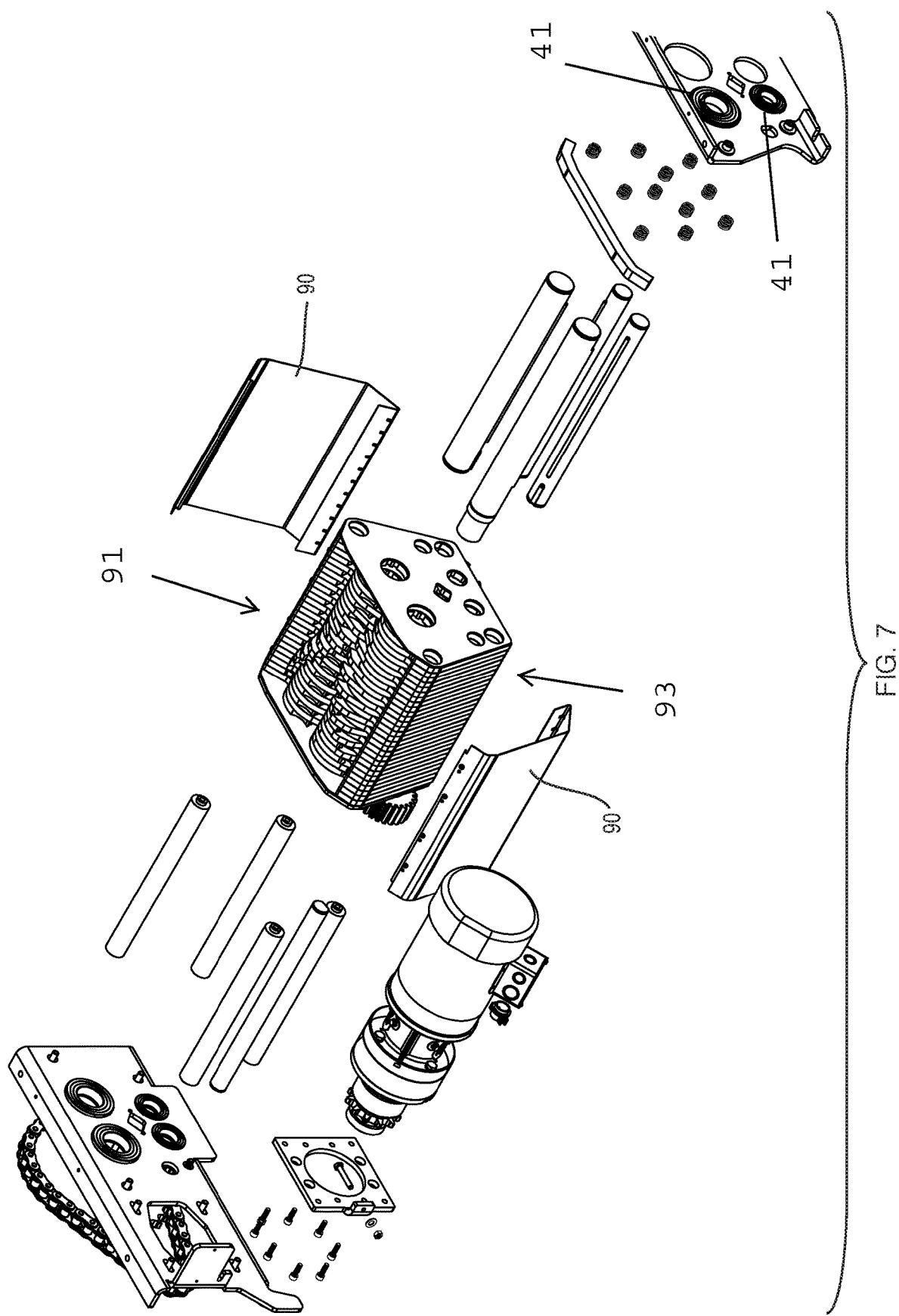

TWO STAGE GRINDER PARTICULARLY SUITABLE FOR MEDICAL WASTE DISPOSAL

This application claims the benefit of U.S. Provisional Application Ser. No. 62/403,430 filed Oct. 3, 2016, the teachings of which are incorporated herein by reference.

FIELD OF INVENTION

The present invention generally relates to a device and an apparatus for grinding of medical waste, such as hypodermic syringes or needles, intravenous (IV) needles and other hazardous medical waste, and more particularly to a two-stage grinder and apparatus embodying same. The invention also relates to methods related thereto.

BACKGROUND OF THE INVENTION

In general, medical waste must be safely collected and disposed of. Medical waste can include, for example, gloves, needles, lancets, syringes, broken glass, scalpels, culture slides, culture dishes, broken capillary tubes, broken rigid plastic, exposed ends of dental wires, stents, laboratory slides and cover slips contaminated with infectious agents. Such medical waste also can be limited to or only include non-sharp medical waste including tubing, gloves, dressings, wipes and the like.

Such medical waste is typically placed in a "sharps container" or a "sharps bin." Such medical waste also can be collected and disposed in other regulated receptacles, containers or bags for biohazard materials. Some examples of such other containers or bags include Regulated Medical Waste Red Bags or Bel-Art Biohazard Bags. Such sharp bins/containers or other biohazard receptacles or bags enable the safe collection, storage and disposal of all categories of sharps waste. Hereinafter reference shall be made to sharp bins or sharp containers for convenience, however, it shall be understood that such reference shall not be limited to those specific bins/containers but shall be inclusive of other manners of collecting and disposing biohazardous or medical waste including other regulated receptacles, containers or bags for such medical waste and/or biohazard materials.

When sharps bins are full or otherwise considered ready for disposal, they are typically removed from the collection location for destruction and disposal offsite. Such disposal is usually by an incineration process.

It thus would be desirable to provide a new device (e.g., a grinding device or grinder) and apparatus embodying such a device, that can render a sharps bin and/or its contents safe for traditional unregulated disposal (e.g., a landfill) after sterilization, as well as methods related thereto. It would be particularly desirable to provide such a device, apparatus and methods related thereto that would be usable as a point of use device/apparatus in comparison to prior art devices/apparatus. Such collection devices preferably would be simple in construction and less costly than prior art devices and such methods would not require highly skilled users to utilize the device.

SUMMARY OF THE INVENTION

The present invention features a device and/or apparatus that can render medical waste and/or the container (e.g., sharp bin/container) or bag containing such medical waste safe for traditional unregulated disposal after sterilization. Such a device includes a two-stage grinder in accordance with the principles of the present invention which two-stage grinder reduces medical waste as well as the receptacle, container or bag for such medical waste, to a particle size to enable safe and efficient disposal in a traditional unregulated disposal site such as a landfill. Further featured is an apparatus embodying such a device as well as methods related thereto.

In more particular aspects/embodiments of the present invention, there is featured a medical waste grinder that includes a first stage, a second stage and a drive system. The first stage includes spring loaded cutter stacks mounted on two adjacent shafts between two edge plates. Each of the cutter stacks includes a plurality of cutters arranged in a helix to create space, each cutter includes a number of teeth per blade and including a major diameter and a minor diameter, each cutter turning opposite a fixed counter knife enabling a pinching action against the teeth of the cutter. The second stage includes spring loaded cutter stacks mounted on two adjacent shafts between the two edge plates. In further embodiments, the drive system is operably coupled to the first and second stages so as to drive each of the first and second stages so as to grind medical waste for disposal.

In more particular embodiments, the drive system comprises a motor (e.g., low horsepower motor), gears and chain or belt drives operably coupled to the motor for torque conveyance such that the first stage drives the second stage through an idler moved by one upper shaft to cause movement of both shafts of the second stage.

In further embodiments, such a medical waste grinder further includes a pair of drip pans mounted on both sides of the first and second stage to prevent leaks through the sides of the cutter stacks.

In more specific embodiments, the cutter stacks are constructed of stainless steel.

In even more particular embodiments, such a medical waste grinder further includes a lubricant system to spray a lubricant between the first stage and the second stage.

According to another aspect of the present invention, there is featured an apparatus that can render a sharps bin and/or its contents safe for traditional unregulated disposal after sterilization. Such an apparatus includes a two-stage grinder designed to reduce the size of medical waste contained in a sharps bin to a particle size after sterilization to enable safe and efficient disposal in a traditional unregulated disposal site.

In more particular embodiments, such an apparatus includes a two stage medical waste grinder as hereinabove described.

Also featured is a method for grinding medical waste that can render a sharps bin and/or its contents safe for traditional unregulated disposal after sterilization.

Other aspects and embodiments of the invention are discussed below.

Definitions

The instant invention is most clearly understood with reference to the following definitions:

USP shall be understood to mean U.S. Patent Number and U.S. Publication No. shall be understood to mean U.S. Published Patent Application Number.

The terms "comprising" and "including": as used in the discussion directed to the present invention and the claims are used in an open-ended fashion and thus should be interpreted to mean "including, but not limited to." Also, the terms "couple" or "couples" is intended to mean either an indirect or direct connection. Thus, if a first component is coupled to a second component, that connection may be through a direct connection, or through an indirect connection via other components, devices and connections. Further the terms "axial" and "axially" generally mean along or substantially parallel to a central or longitudinal axis, while the terms "radial" and "radially" generally mean perpendicular to a central, longitudinal axis.

Additionally, directional terms such as "above," "below," "upper," "lower," etc. are used for convenience in referring to the accompanying drawing figures. In general, "above," "upper," "upward" and similar terms refer to a direction toward a proximal end of an instrument, device, apparatus or system and "below," "lower," "downward," and similar terms refer to a direction toward a distal end of an instrument, device, apparatus or system, but is meant for illustrative purposes only and the terms are not meant to limit the disclosure.

Reference to a singular item, includes the possibility that there are plural of the same items present. More specifically, as used herein and in the appended claims, the singular forms "a," and, "said" and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs.

Medical waste shall be understood to be generally inclusive of material that is or potentially is biohazardous and requiring specific procedures for its safe collection and disposal. Such medical waste can consist of non-sharp medical waste such as tubing, gloves, dressings, wipes and the like. Such medical waste also can include all categories of sharps waste including materials having cutting, piercing or skin penetrating elements. Such sharps medical waste can include, for example, gloves, needles, lancets, syringes, broken glass, scalpels, culture slides, culture dishes, broken capillary tubes, broken rigid plastic, exposed ends of dental wires, stents, laboratory slides and cover slips contaminated with infectious agents.

The term or phrase "sharps container" or a "sharps bin" shall be understood to mean a container, bag, receptacle or other means for the collection and storage of non-sharps medical waste and/or all categories of sharps medical waste for disposal. Such containers, receptacle, bags or other are typically regulated receptacles, containers or bags for biohazard materials such as for example, Regulated Medical Waste Red Bags or Bel-Art Biohazard Bags. The reference made herein in any discussion to sharp bins or sharp containers is done for convenience. Such reference shall not be limited to such bins/containers but shall be inclusive of other manners of collecting and disposing biohazardous or medical waste including other regulated receptacles, containers or bags for biohazard materials.

BRIEF DESCRIPTION OF THE DRAWING

For a fuller understanding of the nature and desired objects of the present invention, reference is made to the following detailed description taken in conjunction with the accompanying drawing figures wherein like reference character denote corresponding parts throughout the several views and wherein:

FIG. 7 is a block diagram of drip pans and other features of the two stage grinder.

DESCRIPTION OF THE PREFERRED EMBODIMENT

Figure 1:
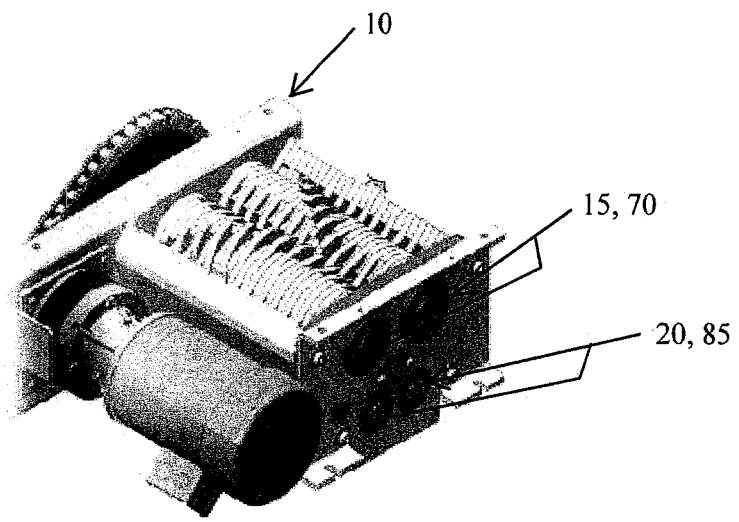
FIG. 1 is a block diagram of an exemplary two stage grinder.

The subject innovation is now described with reference to the drawings, wherein like reference numerals are used to refer to like elements throughout. In the following description, for purposes of explanation, numerous specific details are set forth in order to provide a thorough understanding of the present invention. It may be evident, however, that the present invention may be practiced without these specific details. In other instances, well-known structures and devices are shown in block diagram form in order to facilitate describing the present invention.

There is shown in FIG. 1, an exemplary two-stage grinder 10 in accordance with the principles of the present invention that includes a first stage 15 or first grinding stage and a second stage 20 or second grinding stage. This two-stage design enables the grinding of medical waste to achieve a particle size that is compliant with state and/or federal regulations in the United States. More specifically, a two-stage design that can render a sharps bin and its contents safe for traditional unregulated disposal after sterilization. State regulations vary with a requirement from a particle size of "unrecognizable" to a particle size of "unrecognizable and unusable pieces smaller than three-quarters of an inch, except that all sharps must be smaller than one-half inch."

As described fully herein, such a two-stage grinder 10 is configured an arranged so that medical waste and/or the sharps bin containing such waste is inputted to the first grinding stage 15 for processing thereof to achieve a desired result. The output of the first grinding stage is in turn inputted to the second grinding stage 20 for final processing. In more particular aspects of the present invention such medical waste and the sharps container are sterilized before being inputted to the two-stage grinder 10. In this way, the output of the two-stage grinder can be disposed of in a traditional unregulated disposal site.

As fully described below, in particular embodiments the first stage 15 has two teeth per cutter blade to enable these teeth to grab onto a sharps container. Also and with reference also to FIG. 4, the cutters of the first stage are arranged in a helix to create space for the sharps containers to drop below a major diameter of each cutter. In yet further embodiments, the two-stage grinder 10 can include an aerosol lubricant system that sprays a fine mist between the first stage 15 and the second stage 20.

The two-stage grinder 10 can be integrated into a medical waste disposal system and operate at a slow speed and very high torque to provide balance between input power (e.g., 110 AC, 15 A) and grinding effectiveness.

As shown in FIG. 1, the first stage 15 includes a series (or stack) of rotary cutters on two upper shafts 70 and the second stage 20 includes a series (or stack) of rotary cutters on two lower shafts 85. The rotary cutters of the first stage 15 are designed to grab or capture waste and generate a first reduction in size. The rotary cutters of the second stage 20 generate a second reduction in size that meets or exceeds state or federal particle size requirements for medical waste. More specifically, the second reduction in size preferably reduces the size of the resultant particles of the rendered sharps bin and its contents safe for traditional unregulated disposal after sterilization.

Figure 2A:
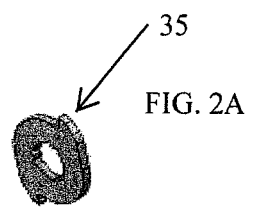
FIG. 2A is a perspective view of an exemplary first stage cutter.
Figure 2B:
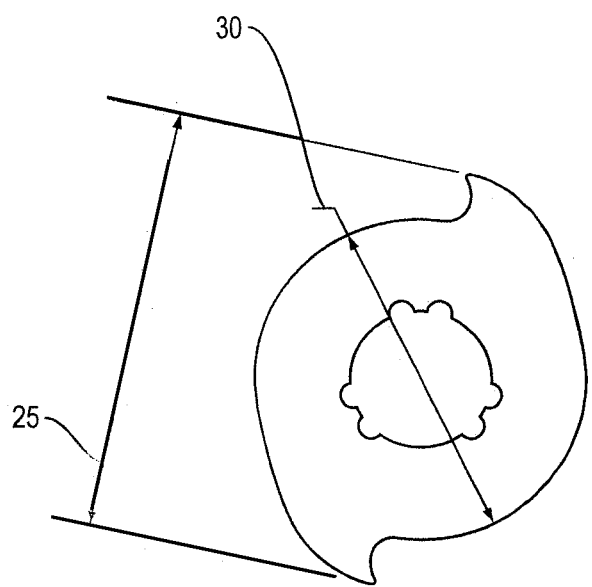
FIG. 2B is a block diagram of an exemplary first stage cutter.
Figure 3:
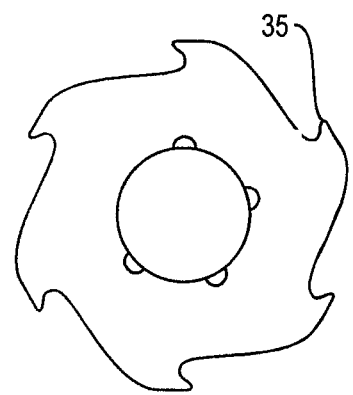
FIG. 3 is a block diagram of an exemplary second stage cutter.
Figure 4:
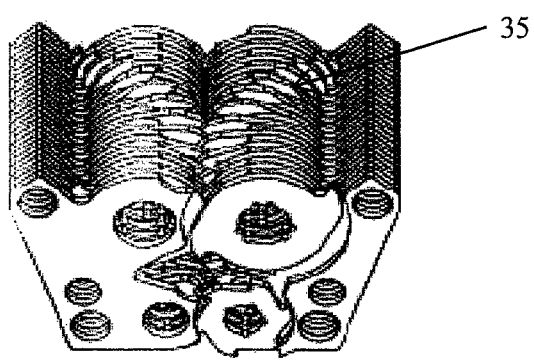
FIG. 4 is block diagram of a helix design of the two stage grinder.
Figure 5:
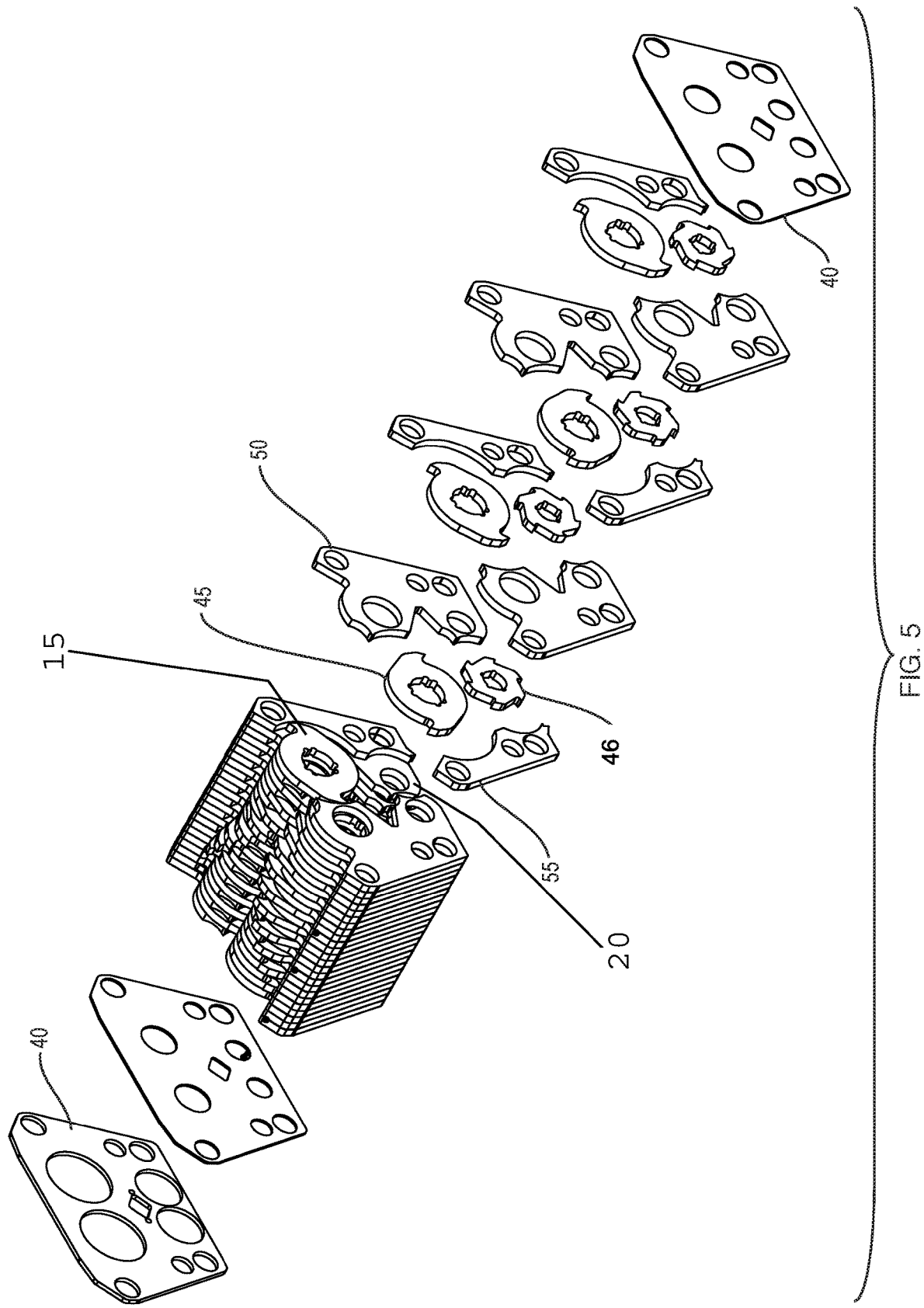
FIG. 5 is a block diagram of spring loading of cutter stacks.
Figure 6:
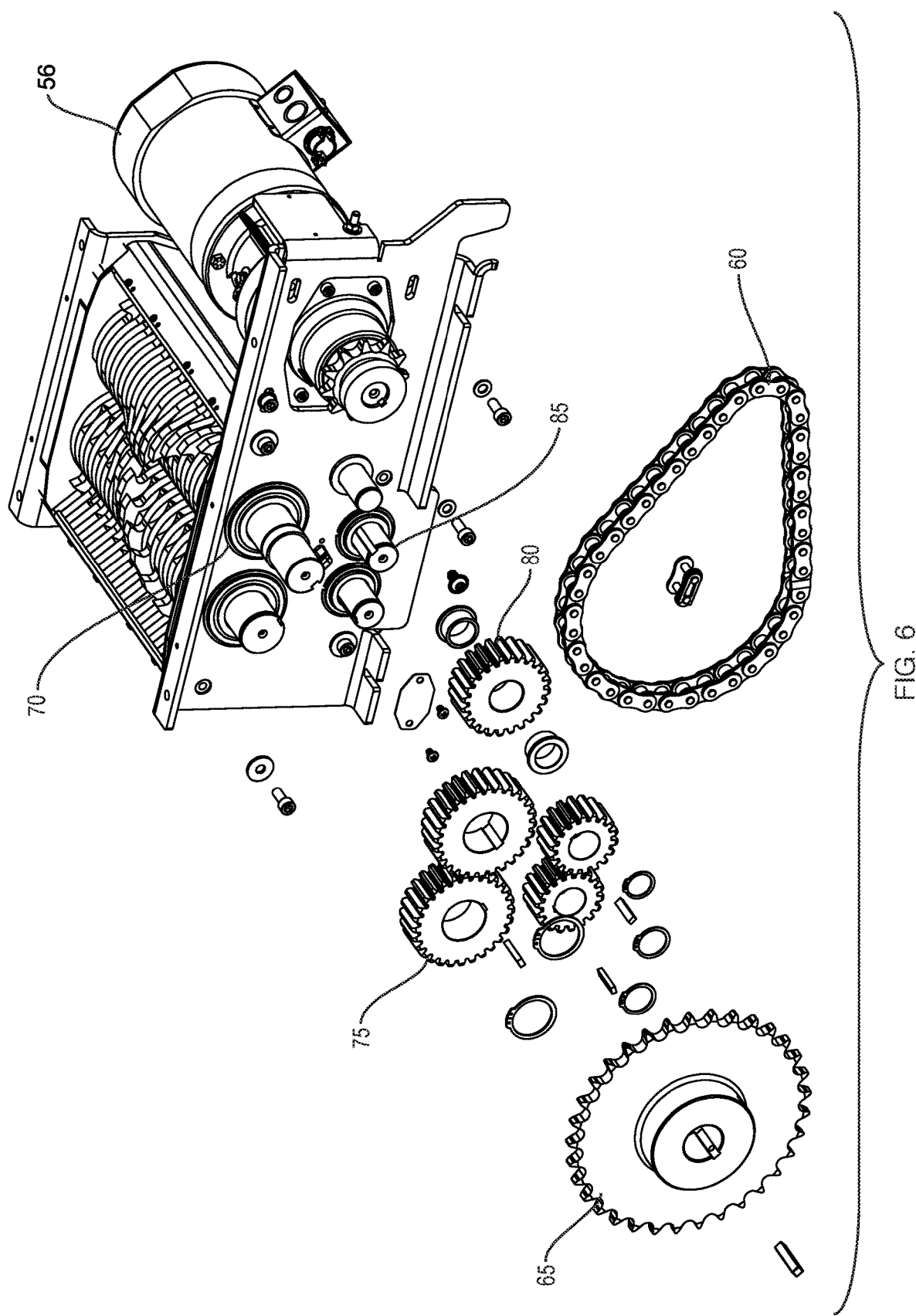
FIG. 6 is a block diagram of a drive system.

More specifically, referring to FIG. 2A, B as well as FIGS. 5-6, a cross-section of each of the rotary cutters in the first stage 15 illustrates the inclusion of a major diameter 25 and a minor diameter 30. The minor diameter is maintained throughout most of the travel of the tooth so that there is an open space for waste to fall down and be grabbed by the teeth; the orientation of the teeth during assembly in a helix configuration promote this (FIG. 4). More specifically, the helix of the teeth 35 promotes capture of waste. FIG. 3 illustrates an exemplary cutter that is used in the second stage 20.

There are two types of cutting action with the design of the teeth in the rotary cutters in the first stage 15. On each of the shafts 70, 85 respectively of the first and second stages 15, 20; there is mounted a stack consisting of a pair of cutters 46, a counter-knife cutter 59, a spacer 55 that is repeated until they fill the shaft. Each of the stacks of both the first stage 15 and the second stage 20 are secured by an edge plate 40 (FIG. 5) that is spring-loaded on their respective shafts and terminated by two end plates positioned on either ends of the shafts with springs 41 as shown in FIG. 7. The spring loading enables, among other things, the cutters along each shaft in the first stage 15 and the second stage 20 to move or float along the shafts.

Having spring loaded cutter stacks also enables cutting in two ways, a scissor cut and a pinching cut. Teeth, running adjacent to each, generate a scissor-like action that enables cutting materials such as rubber gloves, for example. The ends of the teeth are sharpened and each tooth goes against a counter-knife. There is a gap between the tooth and the counter-knife 50 (FIG. 4). A pinching action occurs at a tip to enable cutting materials such as long needle syringes. The number of cutter teeth in the cutter of the second stage 20 outnumber those in the first stage 15 so that waste cannot easily drop between both the first stage 15 and the second stage 20.

As seen in FIG. 5, one counter-knife 50 opposes each cutter 45 in the first stage 15 and its corresponding cutter in the second stage 20.

One objective of the design of the cutters in the first and second stages 15, 20 is to insure no needle passes through unmolested, i.e., that every needle is cut in some fashion and therefore rendered unsuitable for re-use. A similar objective is to render all medical waste that passes through both the first stage 15 and the second stage 20 unrecognizable, i.e., not able to be easily recognized or identified from its original form.

Another objective of the grinder of the present invention is that it is point of use, i.e., installed in an office medical waste disposal/processing system and not part of a massive industrial waste processing system. As such, the grinder emits little or no noise and is powered by a simple residential 110V/220V power outlet found in any home or office. Moreover, the two stage grinder described herein is designed to fit into a point of use medical waste system that is not much bigger than a photocopier in an office reproduction center.

In a preferred embodiment, a motor 56 used to power the grinder of the present invention is typically 1-2 horsepower (hp) or less. As shown in FIG. 6, the motor 56 drives a chain 60 and the chain drives a primary socket. The primary socket operates one upper shaft 70 of the first stage 15, which then through a pair of gears 75, operates the remaining upper shaft 70. The primary shaft also drives an idler 80, which rotates the lower shafts 85 in the second stage 20. In other embodiments, other sizes and types of power sources may be employed as necessary.

The cutter blades are typically constructed of stainless steel because medical waste can be acidic or caustic. In further embodiments, the cutter blades are constructed using any other materials or combination of materials as are otherwise appropriate for the intended use.

As shown in FIG. 7, the two-stage grinder 10 also is configurable so as to include drip pans 90 to prevent leaks through the sides 91, 93 of the cutter stacks and encourage drips to proceed down through the cutter stacks of the first and second stages and into a waste collection system.

While this invention has been particularly shown, and described with references to preferred embodiments thereof, it will be understood by those skilled in the art that various changes in form and details may be made therein without departing from the spirit and scope of the present application as defined by the appended claims. Such variations are intended to be covered by the scope of this present application. As such, the foregoing description of embodiments of the present application is not intended to be limiting.

Incorporation by Reference

All patents, published patent applications and other references disclosed herein are hereby expressly incorporated by reference in their entireties by reference.

Equivalents

Those skilled in the art will recognize, or be able to ascertain using no more than routine experimentation, many equivalents of the specific embodiments of the invention described herein. Such equivalents are intended to be encompassed by the following claims.

What is claimed is:

1. A grinder comprising:
   a first stage, the first stage comprising cutter stacks mounted on two parallel adjacent shafts extending axially between two edge plates, each of the cutter stacks comprising a plurality of cutters arranged in a helix to create a space between the cutter stacks and form an axially moving cutting zone that traverses the space, each cutter comprising a number of teeth per blade and
   including a major diameter and a minor diameter, each cutter turning relative to a fixed counter knife enabling a pinching action against the teeth of the cutter within the axially moving cutting zone;
   the teeth of the major diameter on each shaft being progressively radially offset at acute angles from one another along the length of the shaft to define the helix, the helixes on each adjacent shaft having opposite handedness, with teeth of the helixes being disposed in a scissoring engagement with one another to define the axially moving cutting zone, wherein during operation the helixes are rotated in opposite directions to progressively move the axially moving cutting zone through the space in the axial direction;
   a second stage, the second stage comprising cutter stacks mounted on two adjacent shafts between the two edge plates; and
   a drive system.

2. The grinder of claim 1 wherein the drive system comprises a motor, gears and chain or belt drives operably coupled to the motor for torque conveyance such that the first stage drives the second stage through an idler moved by one upper shaft to cause movement of both shafts of the second stage.

3. The grinder of claim 1 further comprising a pair of drip pans mounted on both sides of the first and second stage to prevent leaks through the sides of the cutter stacks.

4. The grinder of claim 1 wherein the cutter stacks are constructed of stainless steel.

5. A method for processing medical waste comprising the steps of providing the grinder of claim 1, wherein the first stage effects a first reduction in particle size of the medical waste being processed and wherein the second stage effects a second reduction in particle size of the medical waste being processed;
  introducing medical waste into an input of the first stage;
  successively grinding the introduced waste through each of the first and second stages to achieve at least a desired reduction in particulate size of the medical waste;
  sterilizing the medical waste; and
  disposing of the processed medical waste.

6. The method of claim 5, wherein said sterilizing is performed before the medical waste is introduced into the first stage.

7. The method of claim 5, wherein the medical waste to be processed includes a sharps container and the medical waste stored therein.

8. The method of claim 5, wherein said providing further includes providing a point of use two-stage grinder.

9. The method of claim 5, wherein the provided first stage is configured and arranged to grab the medical waste for processing.

10. The grinder of claim 1 wherein the drive system is operably coupled to the first and second stages so as to drive each of the first and second stages to grind the medical waste for disposal.

11. The grinder of claim 1, wherein the cutter stacks are axially spring loaded.

* * * * *